(12) United States Patent  
Pomeranz et al.

(10) Patent No.: US 7,611,530 B2
(45) Date of Patent: Nov. 3, 2009

(54) EXPANDABLE STENT HAVING REMOVABLE SLAT MEMBERS

(75) Inventors: Mark L. Pomeranz, Davie, FL (US); Esteban Pino, Tampa, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 140 days.

(21) Appl. No.: 11/999,394

(22) Filed: Dec. 5, 2007

(65) Prior Publication Data

US 2008/0091260 A1    Apr. 17, 2008

Related U.S. Application Data

(62) Division of application No. 10/696,667, filed on Oct. 29, 2003, now abandoned.

(51) Int. Cl.
*A61F 2/06* (2006.01)
(52) U.S. Cl. .................... 623/1.13; 623/1.15; 623/1.32; 623/1.44; 623/1.51
(58) Field of Classification Search .................. 623/1.1, 623/1.13, 1.15, 1.16, 1.2, 1.32, 1.33, 1.44, 623/1.51; 606/191, 194, 198
See application file for complete search history.

(56) References Cited

U.S. PATENT DOCUMENTS

| | | | |
|---|---|---|---|
| 4,743,252 A | 5/1988 | Martin, Jr. et al. | |
| 4,743,352 A | 5/1988 | Watkins-Pitchford | |
| 5,064,435 A | 11/1991 | Porter | |
| 5,100,429 A | 3/1992 | Sinofsky et al. | |
| 5,342,348 A * | 8/1994 | Kaplan | 604/891.1 |
| 5,609,628 A | 3/1997 | Keranen | |
| 5,665,063 A | 9/1997 | Roth et al. | |
| 5,702,418 A | 12/1997 | Ravenscroft | |
| 5,713,917 A | 2/1998 | Leonhardt et al. | |
| 5,741,325 A | 4/1998 | Chaikof et al. | |
| 5,749,919 A | 5/1998 | Blanc | |
| 5,755,773 A | 5/1998 | Evans et al. | |
| 5,769,884 A | 6/1998 | Solovay | |
| 5,921,954 A | 7/1999 | Mohr, Jr. et al. | |
| 5,951,599 A | 9/1999 | McCrory | |
| 6,004,261 A | 12/1999 | Sinofsky et al. | |
| 6,030,414 A | 2/2000 | Taheri | |
| 6,102,938 A | 8/2000 | Evans et al. | |
| 6,254,628 B1 | 7/2001 | Wallace et al. | |
| 6,290,673 B1 | 9/2001 | Shanley | |
| 6,395,018 B1 | 5/2002 | Astaneda | |
| 6,497,722 B1 | 12/2002 | Von Oepen et al. | |
| 6,524,335 B1 | 2/2003 | Hartley et al. | |
| 6,569,195 B2 | 5/2003 | Yang et al. | |
| 6,605,111 B2 | 8/2003 | Bose et al. | |
| 6,673,106 B2 | 1/2004 | Mitelberg et al. | |

(Continued)

*Primary Examiner*—Todd E Manahan
*Assistant Examiner*—Katherine M Dowe

(57) ABSTRACT

A medical device having at least one expandable stent, and at least three removable slat members carried by the stent. The removable slat members provide a substantially continuous cover for the medical device, and thus impede the flow of blood through the peripheral walls of the medical device. When deployed within a blood vessel, some of the slat members may serve to cover an aneurysm and restrict the blood flow into the aneurysm. In addition, one or more of the slat members may be selectively removed to provide blood flow into a branching blood vessel. In an alternative embodiment, an inner expandable stent is coaxially disposed within the outer expandable stent, and three removable slat members are carried by the inner expandable stent.

12 Claims, 7 Drawing Sheets

U.S. PATENT DOCUMENTS

| | | |
|---|---|---|
| 6,833,003 B2 | 12/2004 | Jones et al. |
| 7,147,659 B2 | 12/2006 | Jones |
| 7,156,871 B2 | 1/2007 | Jones et al. |
| 2002/0035394 A1 | 3/2002 | Fierens et al. |
| 2002/0072790 A1 | 6/2002 | McGuckin, Jr. et al. |
| 2002/0072792 A1 | 6/2002 | Burgermeister et al. |
| 2002/0128706 A1 | 9/2002 | Osypka |
| 2002/0193872 A1 | 12/2002 | Trout, III et al. |
| 2002/0193873 A1 | 12/2002 | Brucker et al. |
| 2003/0074049 A1 | 4/2003 | Hoganson et al. |
| 2003/0109917 A1 | 6/2003 | Rudin et al. |
| 2003/0135265 A1 | 7/2003 | Stinson |
| 2003/0139802 A1 | 7/2003 | Wulfman et al. |
| 2003/0153972 A1 | 8/2003 | Helmus |
| 2003/0208256 A1 | 11/2003 | DiMatteo et al. |
| 2003/0216804 A1 | 11/2003 | Debeer et al. |
| 2004/0006381 A1 | 1/2004 | Sequin et al. |
| 2004/0044396 A1 | 3/2004 | Clerc et al. |

* cited by examiner

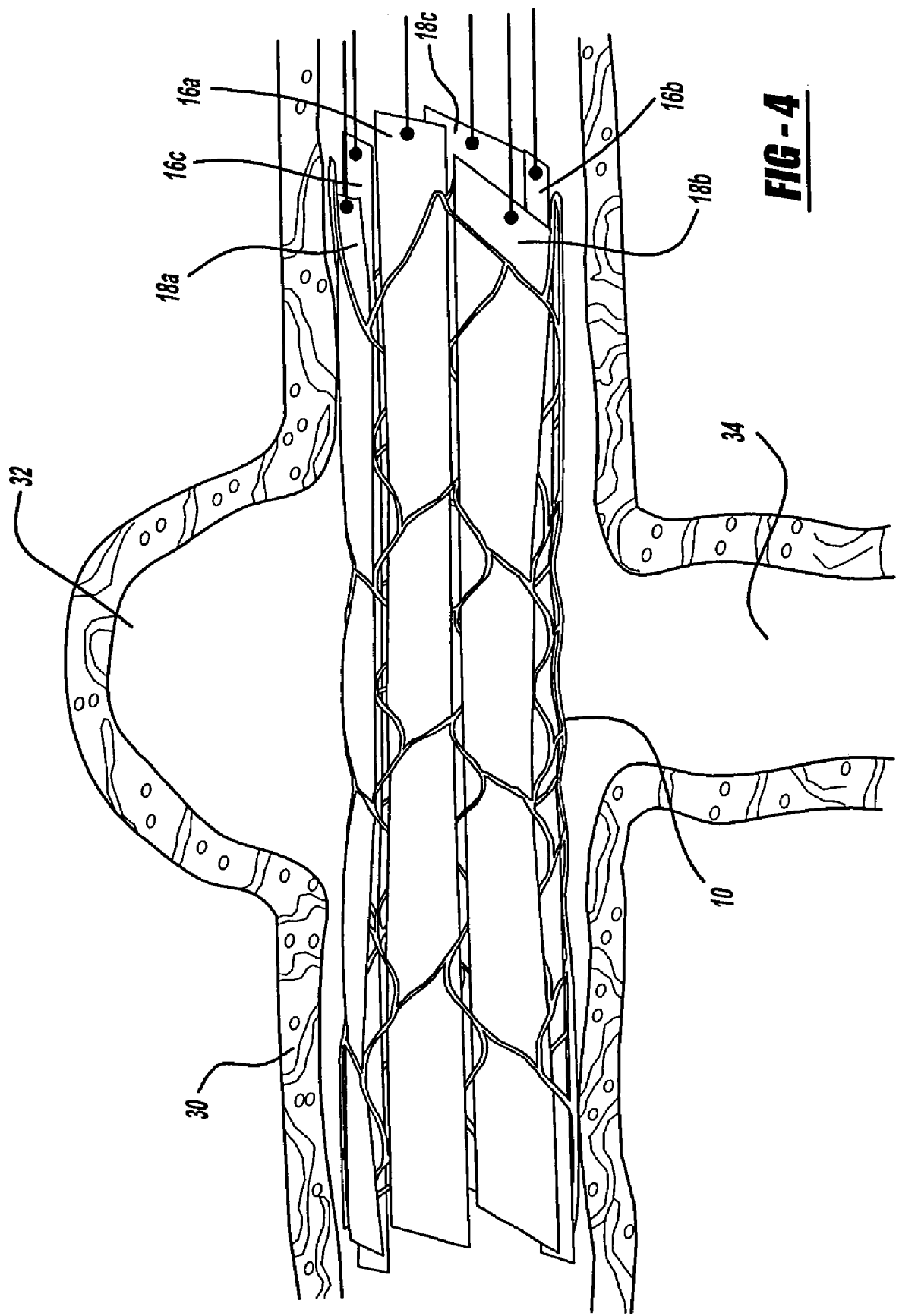

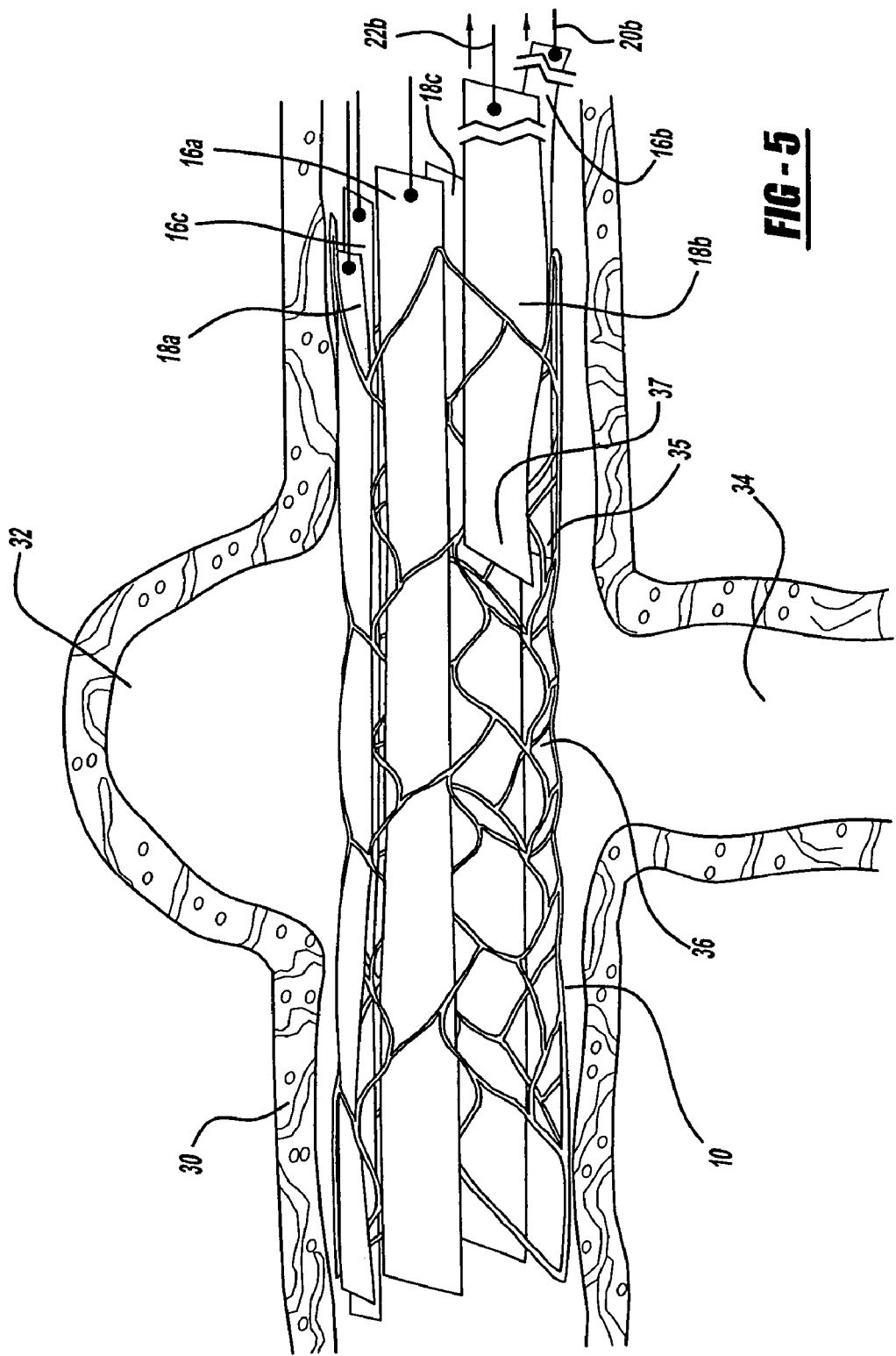

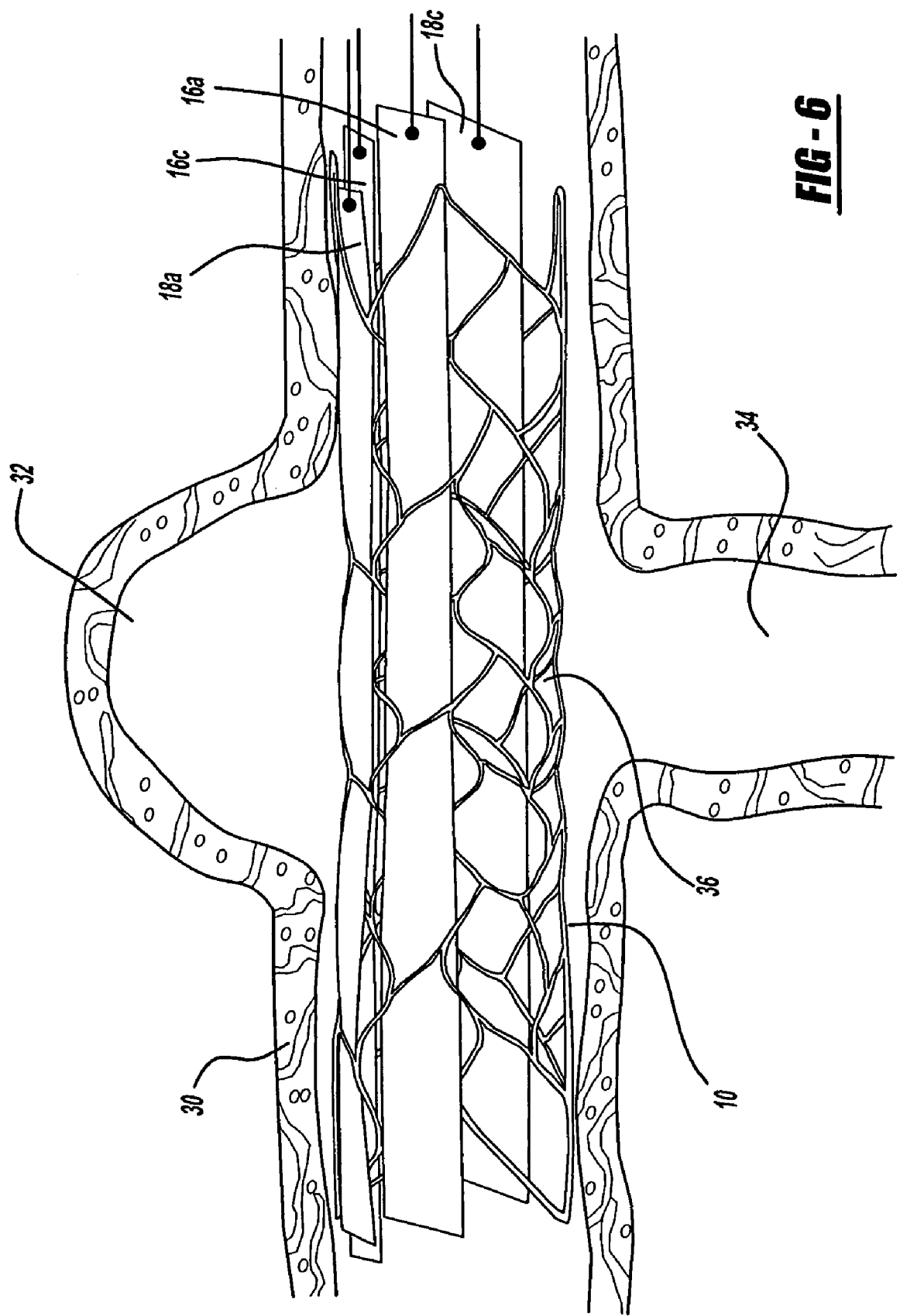

EXPANDABLE STENT HAVING REMOVABLE SLAT MEMBERS

REFERENCE TO RELATED APPLICATION

This patent application is a divisional of U.S. patent application Ser. No. 10/696,667 entitled "Expandable Stent Having Removable Slat Members", filed Oct. 29, 2003 now abandoned.

BACKGROUND OF INVENTION

1. Field of the Invention

The present invention relates to intravascular stents and methods of treating aneurysms, and more particularly, this invention relates to a covered stent which may be modified to treat an aneurysm located adjacent to a bifurcated blood vessel while permitting blood to flow through the bifurcated vessel and method of use thereof.

2. Description of the Prior Art

Expandable stents are widely used in the treatment of vascular diseases. Typically, a stent is inserted into a stenosed blood vessel after an angioplasty to prevent the restenosis of the blood vessels. Expandable stents are also used as aneurysm covers. When a stent is placed across an aneurysm, the blood flow into the aneurysm is decreased. Decreased blood flow within an aneurysm promotes the formation of a thrombus within the aneurysm which ultimately aids in protecting the aneurysm from further expansion or rupture.

Optimally, a covered stent is positioned across an aneurysm to completely restrict the blood flow into the aneurysm. Such covered stents, typically covered with a material such as PTFE provide suitable aneurysm covers; however, these stents have certain limitations. For example, covered stents impede blood flow into branching blood vessels. Thus, a covered stent may not be suitable for treating an aneurysm at or near a bifurcated blood vessel.

Several patents and patent applications disclose covered stents with various modifications which tend to avoid these limitations inherent with typical covered stents. For example, U.S. Pat. No. 6,030,414, entitled "Variable Stent and Method for Treatment of Arterial Disease," discloses a covered stent having predetermined and sized lateral openings for the treatment of arterial disease at or around the intersection of multiple arteries; U.S. Pat. No. 6,497,722, entitled "Method and Apparatus for In-Vivo Tailored Stents Indicated For Use in Tortuous Anatomy," discloses a stent having a side opening to allow unimpeded blood flow to a branching vessel at the point of stenting; and, U.S. Patent Application Publication No. 2003/0074049, entitled "Covered Stents and Systems for Deploying Covered Stents," discloses a covered stent which may be perforated in order to allow blood flow into a side branch or bifurcated vessel.

SUMMARY OF THE INVENTION

In accordance with one aspect of the present invention, there is provided a medical device comprising an expandable stent which takes the form of a small diameter skeletal tubular member having a thin wall. The wall of the skeletal tubular member includes a plurality of cells which are formed by a plurality of interconnected strut members. Additionally, the medical device includes an elongated removable slat member interwoven between at least two of the plurality of strut members. The removable slat member is temporarily attached to the skeletal tubular member and provides a cover for a portion of the wall of the tubular member by impeding the flow of blood through that portion of the wall of the tubular member. Alternatively, the medical device includes a plurality of elongated removable slat members interwoven between the strut members of the expandable stent to form a continuous cover around the periphery of the stent.

The medical device further includes a plurality of tethers, each of which are removably attached to one of the plurality of removable slat members in order to selectively remove any one of the slat members from the stent. By removing a slat member, a physician may selectively provide a passage of blood through the wall of the stent. Preferably, the tethers are coated with a radiopaque material so that the tether attached to a selected removable slat member may be identified under fluoroscopy. Alternatively, the tethers are formed from a bioabsorbable material so that the tethers which are not removed with their corresponding slat member will biodegrade and be absorbed by the body.

In accordance with still another aspect of the present invention, there is provided a medical device comprising an expandable stent which takes the form of a hollow tubular member comprised of an expandable wire frame. Additionally, the medical device includes an elongated removable slat member carried by the expandable wire frame. The removable slat member provides a cover for a portion of the peripheral surface of the expandable wire frame and impedes the flow of blood through that portion of the peripheral surface. Preferably, a tether is attached to the proximal end of the removable slat member. In addition, the tether is removably attached to the slat member so that if the slat member is not to be subsequently removed, the tether may be detached from the slat member and removed from the body.

In accordance with another aspect of the present invention, there is provided a medical device comprising an expandable stent which takes the form of a small diameter skeletal tubular member having a thin wall. The wall of the skeletal tubular member includes a plurality of cells which are formed by a plurality of interconnected strut members. The medical device also includes a detachable section. The detachable section is temporarily attached to the skeletal tubular member and provides a cover for a portion of the wall of the tubular member by impeding the flow of blood through that portion of the wall of the tubular member. Upon removal of the detachable section from the wall of the stent, blood is permitted to flow out of the portion of the wall which was covered by the detachable section.

In accordance with a further aspect of the present invention, there is provided a medical device having an outer expandable stent which takes the form of a first hollow skeletal tubular member comprised of a first expandable wire frame, and a first plurality of removable slat members carried by the first expandable wire frame. The first plurality of removable slat members are preferably spaced apart at approximately equal distances along the first peripheral surface of the first skeletal tubular member to thereby cover a portion of the first peripheral surface of the first skeletal tubular member. The medical device further includes an inner expandable stent which takes the form of a second hollow skeletal tubular member having an inner expandable wire frame, and a second plurality of removable slat members carried by the second expandable wire frame. The second plurality of removable slat members are space apart at approximately equal distances along the second peripheral surface of the second skeletal tubular member to thereby cover a portion of the second peripheral surface of the second skeletal tubular member. The inner expandable stent is coaxially disposed within the outer expandable stent and is oriented with respect to the outer expandable stent such that the first plurality of slat members and the second plurality of slat members form substantially a continuous cover for the medical device. Preferably, the medical device includes a plurality of tethers. Each of said plurality of tethers is attached to one of the plurality of slat members in order to remove a selected one of the slat members from the medical device.

In accordance with still another aspect of the present invention, there is provided a medical device having an outer expandable stent. The outer expandable stent takes the form of a first hollow skeletal tubular member comprised of a first plurality of cells formed by a first plurality of interconnected strut members, and a first plurality of removable slat members interwoven between the first plurality of strut members along the first longitudinal axis of the first skeletal tubular member. The first plurality of removable slat members are spaced apart at approximately equal distances along the first peripheral surface of the first skeletal tubular member to thereby cover a portion of the first peripheral surface of the first skeletal tubular member. The medical device further includes an inner expandable stent which takes the form of a second hollow skeletal tubular member comprised of a second plurality of cells formed by a second plurality of interconnected strut members, and a second plurality of removable slat members interwoven between the second plurality of strut members along the second longitudinal axis of the second skeletal tubular member. The second plurality of removable slat members are space apart at approximately equal distances along the second peripheral surface of the second skeletal tubular member to thereby cover a portion of the second peripheral surface of the second skeletal tubular member. The inner expandable stent is coaxially disposed within the outer expandable stent and oriented with respect to the outer stent such that the first plurality of slat members and the second plurality of slat members form substantially a continuous cover for the medical device. In addition, the medical device includes a plurality of detachable tethers, each attached to one of the slat members in order to remove a selected one of the slat members from the medical device.

In accordance with another aspect of the present invention, there is provided a method of treating an aneurysm. The method includes the steps of inserting a covered stent into a blood vessel of a patient, positioning the covered stent adjacent to a diseased portion of the blood vessel such as an aneurysm, and removing and withdrawing a detachable portion of the side wall of the covered stent. By removing the detachable portion of the sidewall of the covered stent, blood may flow through that portion of the wall of the stent and into surrounding blood vessels which branch from the main blood vessel.

In accordance with still another aspect of the present invention, there is provided a method of treating an aneurysm. The method includes the steps of inserting an expandable stent having removable side slat members into a blood vessel of a patient, advancing the expandable stent distally through the blood vessel until the stent is aligned with and covering an aneurysm in the blood vessel, and selectively removing any one of the removable slat members. By removing the slat member, blood is permitted to flow through the peripheral surface of the stent and into branching blood vessels while maintaining a covering for the aneurysm.

BRIEF DESCRIPTION OF THE DRAWINGS

FIG. 4 is an enlarged view of the medical device deployed within a blood vessel and positioned across an aneurysm at a vessel bifurcation prior to removal of any slat member;

FIG. 5 illustrates the medical device within a blood vessel after partial removal of two slat members; and, FIG. 6 shows the medical device having two slat members fully removed in order to permit blood flow into a branching blood vessel.

DESCRIPTION OF THE PREFERRED EMBODIMENT

Figure 1:
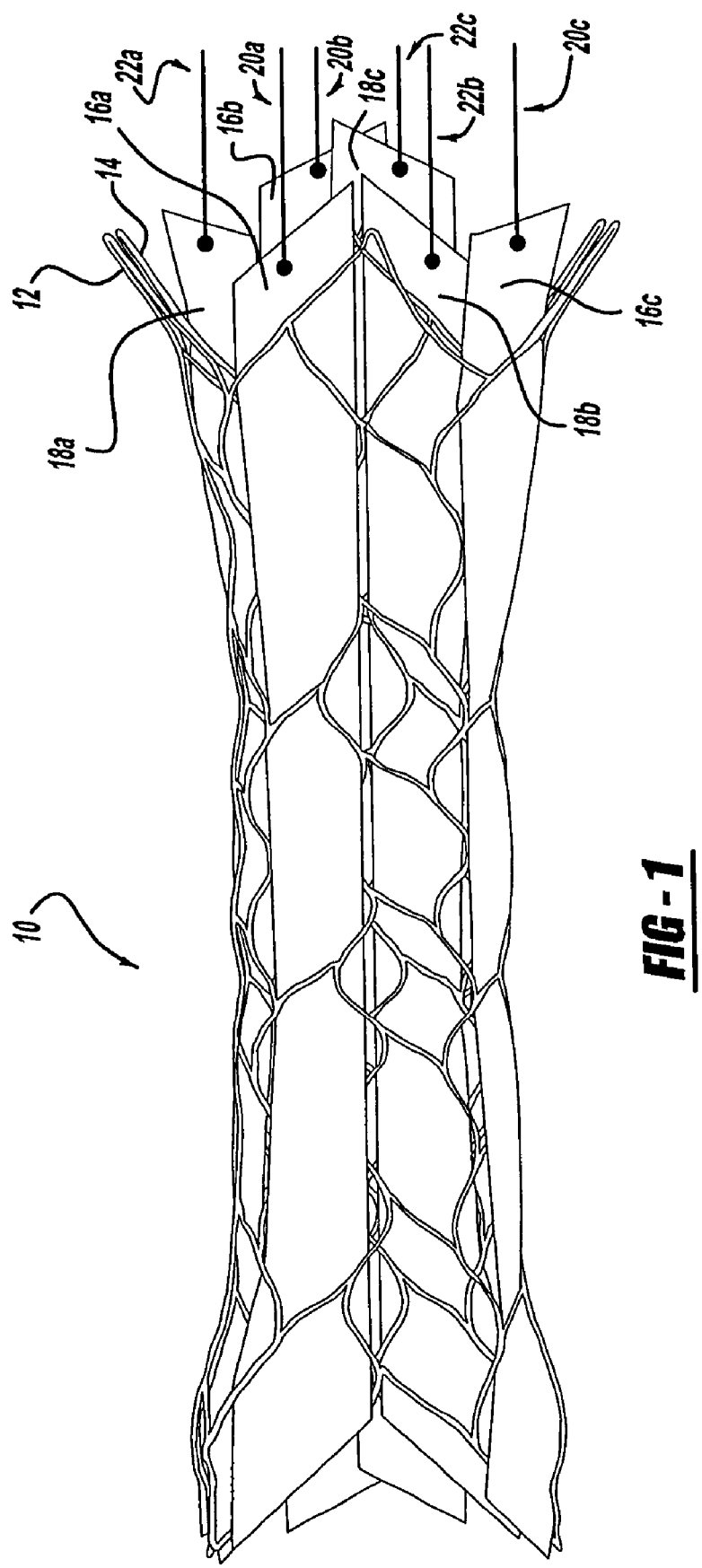
FIG. 1 is an enlarged elevational view of a medical device comprised of an outer and an inner expandable stent each having three removable slat members.

FIG. 1 illustrates a medical device 10 which may be used to treat an aneurysm, such as an aneurysm within the brain, occurring in a blood vessel at or near a bifurcation in the blood vessel. In the preferred embodiment of the present invention, the medical device 10 is comprised of an outer expandable stent 12 and an inner expandable stent 14 coaxially disposed within the outer expandable stent 12. Additionally, the medical device 10 includes a first plurality of removable slat members 16a, 16b, 16c carried by the outer expandable stent 12 and a second plurality of removable slat members 18a, 18b, 18c carried by the inner expandable stent 14.

The medical device 10, as illustrated, includes a total of six removable slat members, but it should be appreciated that the medical device 10 may include more or less slat members depending upon the size of the stent and the application of the device. The removable slat members 16a, 16b, 16c, 18a, 18b, and 18c are preferably formed of a material such as PTFE, often used in grafts, but may be formed of other polymeric or metallic materials. Attached to the proximal portion of each removable slat member 16a, 16b, 16c is one of a first set of detachable tethers 20a, 20b, 20c, respectively, and attached to the proximal portion of each of the other removable slat members 18a, 18b, 18c is one of a second set of detachable tethers 22a, 22b, 22c, respectively.

Figure 2:
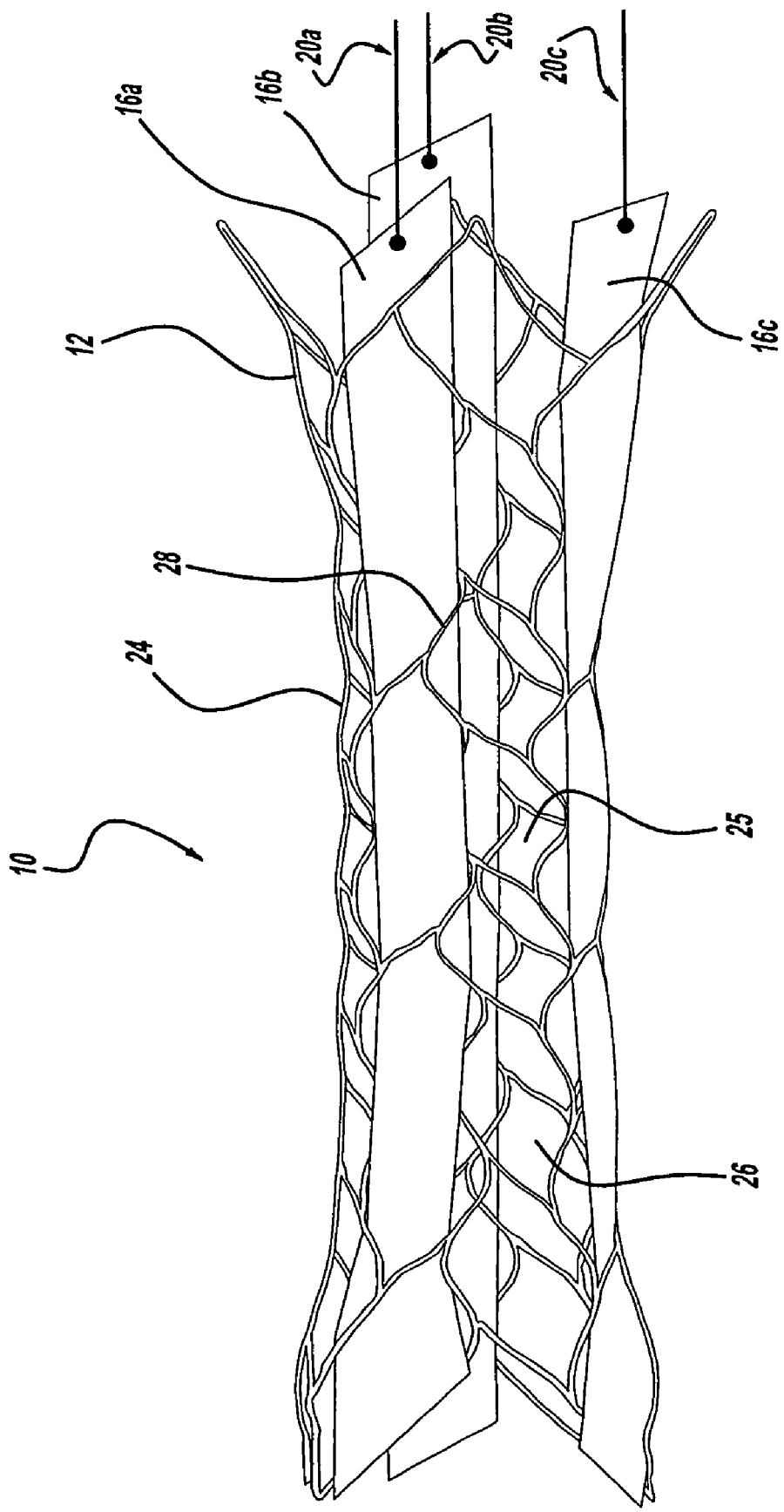
FIG. 2 is an enlarged elevational view of the outer expandable stent only with three removable slat members.

For illustrative purposes only, FIG. 2 illustrates the medical device 10 without the inner expandable stent 14. The inner expandable stent 14 is identical to the outer expandable stent 12, except that it is of a slightly smaller diameter. The outer expandable stent 12 takes the form of a hollow skeletal tubular member comprised of an expandable wire frame 24. The wire frame 24 is preferably formed of Nitinol material and is thereafter heat-treated so as to exhibit superelastic properties at body temperature. Alternatively the wire frame may be formed of other metallic or polymeric materials. The peripheral surface 25 of the wire frame 24 is comprised of a plurality of cells 26 which are formed by a plurality of interconnected strut members 28 which may take on many different patterns and configurations. Examples of such patterns and configurations are disclosed in U.S. patent applications Ser. Nos. 10/163,116; 10/163,248; and 10/425,380, entitled "Intravascular Stent Device," filed on Jun. 5, 2002, Jun. 5, 2002 and Apr. 29, 2003, respectively, and assigned to the same assignee as the present patent application. Alternatively, the wire frame 24 may take the form of a simple helically wound coil. Interwoven between the interconnected strut members 28 of the outer expandable stent 12 are three removable slat members 16a, 16b, 16c. The removable slat members 16a, 16b, 16c provide a cover for a portion of the peripheral surface 25 of the wire frame 24. When implanted into a blood vessel, the covered portion of the outer stent 12 will impede blood flow through the surface 25 of the outer stent 12.

Attached to the proximal section of each removable slat member 16a, 16b, 16c is one of a plurality of detachable tethers 20a, 20b, 20c. The detachable tethers 20a, 20b, 20c are used to aid in the removal of the slat members 16a, 16b, 16c once the stent has been placed into a blood vessel. The detachable tethers 20a, 20b, 20c preferably take the form of a stainless steel wire coated with a radiopaque material. Alternatively, the detachable tethers 20a, 20b, 20c may be formed of a bioabsorbable polymeric material. Additionally, the detachable tethers 20a, 20b, 20c may be detached from the removable slat members 16a, 16b, 16c by mechanical, chemical, or electromagnetic means.

Figure 3A:
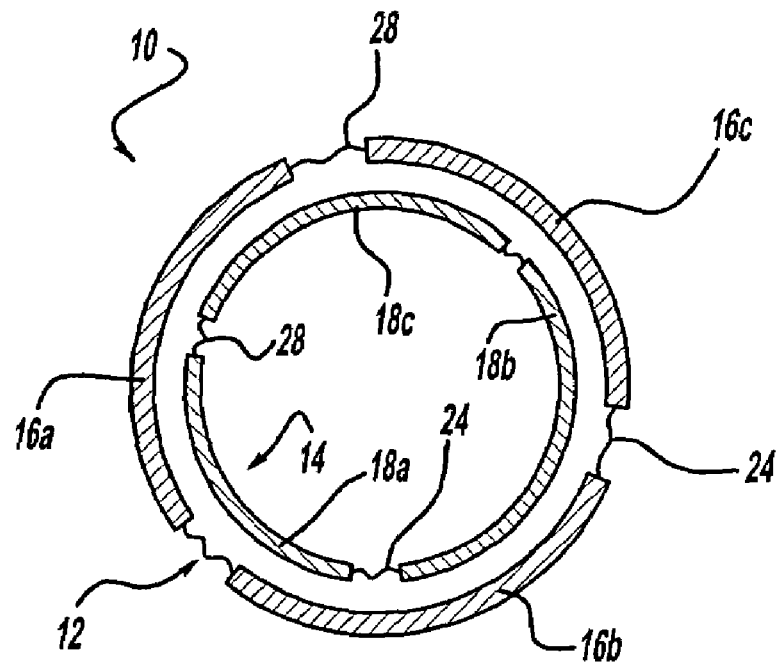
FIG. 3a, FIG. 3b, and FIG. 3c are enlarged cross-sectional views of the medical device illustrated in FIG. 1 illustrating an inner and outer expandable stent and slat members carried by the stents prior to expansion, upon expansion, and upon removal of two slat members, respectively.
Figure 3B:
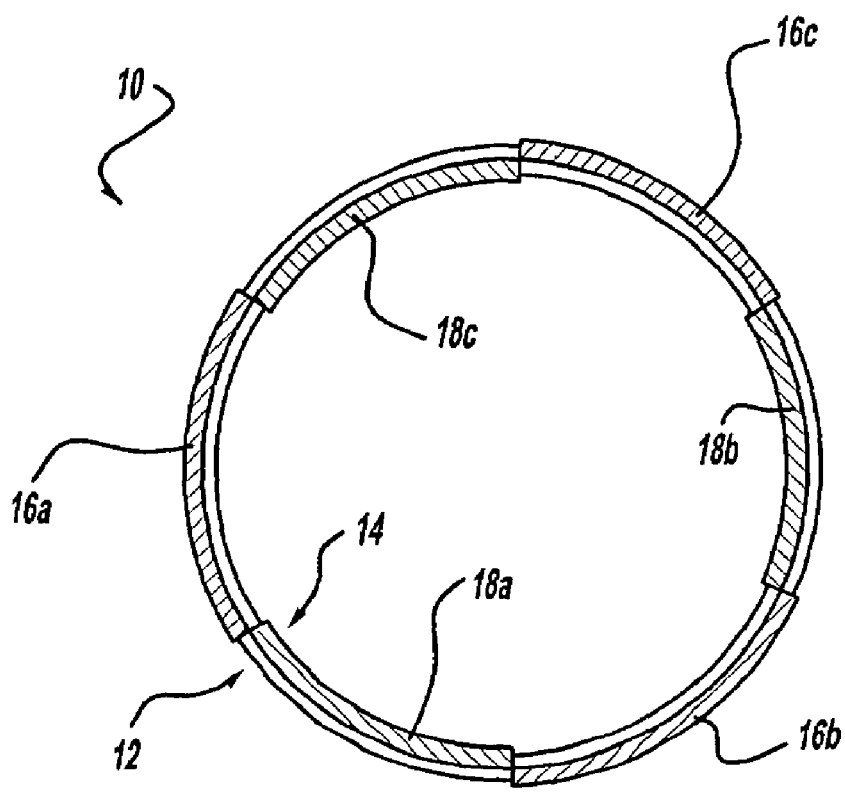
Figure 3C:
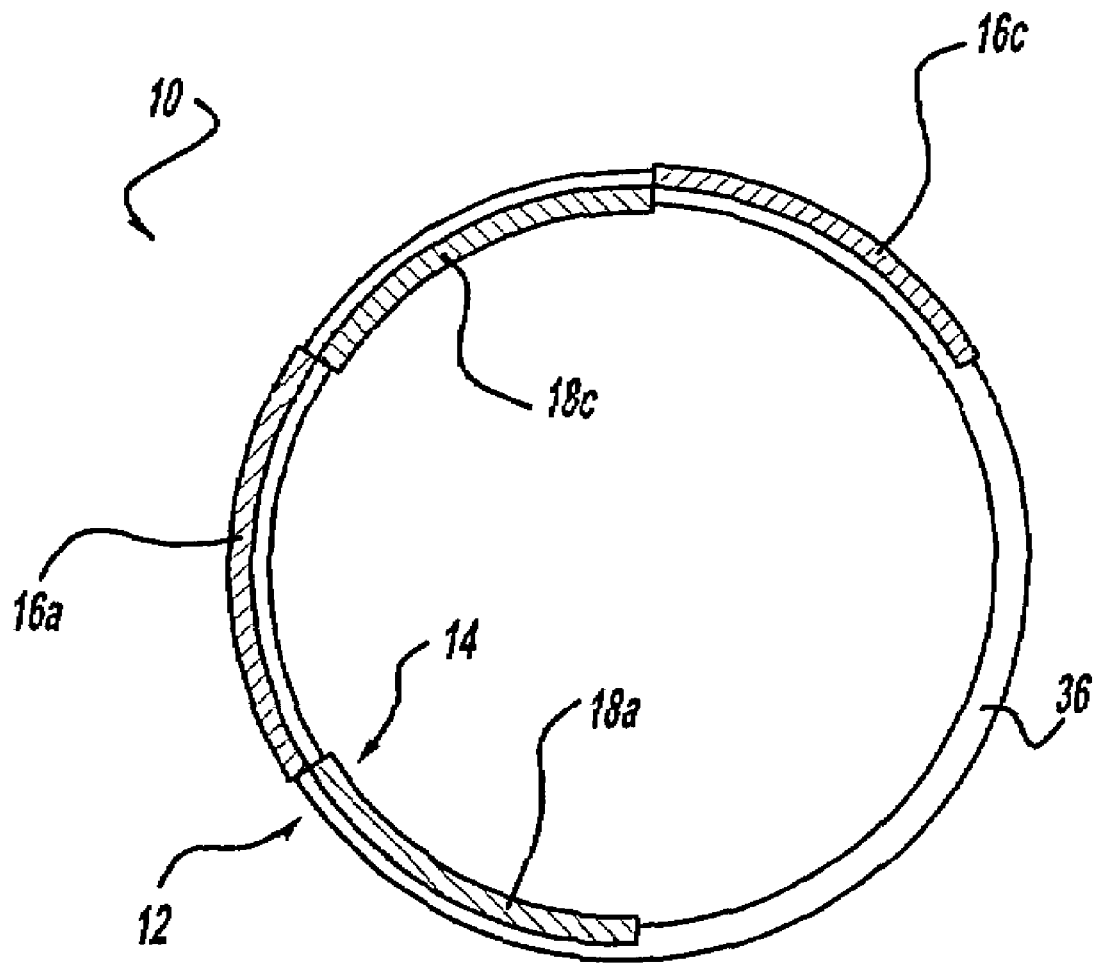

FIGS. 3a, 3b, and 3c show cross-sectional views of the medical device 10. In FIG. 3a, the medical device 10 is in a compressed state. While in a compressed state, the medical device 10 may be delivered to a diseased blood vessel using a catheter-based delivery system. As shown, the inner expandable stent 14 is coaxially disposed within the outer expandable stent 12. The first plurality of removable slat members 16a, 16b, 16c are carried by the wire frame 24 of the outer expandable stent 12. The removable slat members 16a, 16b, 16c are preferably interwoven between the strut members 28 of the outer expandable stent 12. Similarly, the second plurality of removable slat members 18a, 18b, 18c are carried by the wire frame 24 of the inner expandable stent 14 and are preferably interwoven between the strut members 28 of the inner expandable stent 14.

The inner expandable stent 14 is aligned within the outer expandable stent 12 such that when expanded, as shown in FIG. 3b, the removable slat members 16a, 16b, 16c, 18a, 18b, and 18c form a continuous cover for the medical device 10. When the medical device 10 is deployed within a blood vessel, the removable slat members 16a, 16b, 16c, 18a, 18b, and 18c impede the flow of blood through the peripheral surface of the medical device. By removing one of the slat members 16a, 16b, 16c, 18a, 18b, and 18c, an opening would be provided through the portion of the medical device 10 covered by the removed slat member. Thus, a physician may re-establish patency in a branching blood vessel while impeding blood flow through other portions of the medical device 10.

FIG. 3c shows a cross-sectional view of the medical device 10 having two removable slat members 16b, 18b removed from the medical device. The removal of the slat members 16b, 18b uncovers a portion of the peripheral surfaces of the expandable stents 12, 14. Thus, an opening 36 is formed for which blood may flow through the medical device 10 and into branching blood vessels.

FIG. 4 illustrates a medical device 10 positioned adjacent an aneurysm 32 at a bifurcation of a blood vessel 30 within the brain of a patient. The removable slat members 16a, 16b, 16c, 18a, 18b, and 18c cover the medical device 10 and block the flow of blood through the peripheral surface of the medical device. As shown, the medical device 10 prevents blood flow into the adjacent aneurysm 32. By restricting the blood flow into the aneurysm 32, thrombus forms within the aneurysm and the pressure on the wall of the aneurysm is relieved; however, the blood flow to a branching blood vessel 34 has also been restricted.

FIG. 5 shows how patency to the branching blood vessel 34 is re-established. The detachable tether 20b is moved proximally, thereby pulling removable slat member 16b proximally through the medical device 10. When the distal end 35 of the removable slat member 16b is moved past the branching blood vessel 34, blood flow returns to the branching blood vessel through the opening 36 through the peripheral surface of the medical device 10. Additionally, the removable slat member 18b is removed by pulling the detachable tether 22b proximally until the distal end 37 of the slat member 18b has passed the branching blood vessel 34. The removal of the slat member 18b further uncovers the medical device 10 and allows for increased blood flow into surrounding blood vessels. In this fashion, patency may be re-established to surrounding blood vessels while still covering the aneurysm 32.

Illustrated in FIG. 6 is the medical device 10 deployed within the bifurcated blood vessel 30 and having two slat members 16b, 18b removed from the medical device. The remaining slat members 16a, 16c, 18a, and 18c cover the portion of the medical device 10 which is adjacent to the aneurysm 32. As shown, blood may flow through the opening 36 in the medical device 10, but blood may not flow into the aneurysm 32.

Also provided is a method of treating an aneurysm including the steps of inserting the medical device 10 into the diseased blood vessel 30 of a patient, advancing the medical device distally through the blood vessel until the medical device is aligned with and covering an aneurysm 32 in the blood vessel, and selectively removing any one of the plurality of removable slat members 16a, 16b, 16c, 18a, 18b, and 18c by moving the tether 20a, 20b, 20c, 22a, 22b, and 22c attached to the selected slat member proximally and thus allowing blood flow through the peripheral surface of the medical device and into a branching blood vessel 34.

A novel medical device and method to treat an aneurysm at a bifurcation has been disclosed. Although a preferred embodiment of the present invention has been described, it should be understood that various modifications such as for example removal of the detachable section by an electrical or electrolytic process, by a hydraulic process or by other mechanical processes may be made by one skilled in the art without departing from the scope of the claims which follow.

That which is claimed is:

1. A vascular medical device for use in a blood vessel of a patient comprising:
    an expandable stent which takes the form of a small diameter skeletal tubular member having a thin wall, said wall of said skeletal tubular member including a plurality of cells which are formed by a plurality of interconnected strut members;
    a plurality of elongated removable slat members interwoven between at least two of said plurality of strut members to temporarily attach said plurality of said removable slat members to said skeletal tubular member to thereby provide a substantially continuous cover for the peripheral surface of said skeletal tubular member such that said substantially continuous cover impedes the flow of blood through the peripheral surface of said medical device when deployed within the blood vessel, wherein each slat member has a circumferential width greater than its wall thickness; and
    a plurality of tethers each attached to one of said plurality of removable slat members in order to selectively remove any one of said removable slat members to thereby provide a selective passage for blood flow through a portion of the wall of said skeletal tubular member to re-establish patency in a branching vessel while impeding blood flow through other portions of said medical device.

2. The vascular medical device as defined in claim 1, wherein said tethers are removably attached to the removable slat members.

3. The vascular medical device as defined in claim 1, wherein said tethers take the form of elongated puller wires.

4. The vascular medical device as defined in claim 1, wherein said tethers are comprised of a bioabsorbable material.

5. The vascular medical device as defined in claim 1, further comprising:
- an inner expandable stent which takes the form of a second hollow skeletal tubular member which defines a second peripheral surface;
- a second plurality of removable slat members carried by said second skeletal tubular member and spaced apart at approximately equal distances around the second peripheral surface of said second skeletal tubular member to thereby provide a substantially continuous cover for said second peripheral surface, said second skeletal tubular member being coaxially disposed within said skeletal tubular member and being oriented such that said pluralities of removable slat members form a substantially continuous cover for said medical device, wherein each slat member has a circumferential width greater than its wall thickness; and
- a second plurality of tethers each attached to one of said second plurality of removable slat members in order to selectively remove any one of said second plurality of slat members to thereby provide a selective passage for blood flow through the second peripheral surface.

6. The vascular medical device as defined in claim 5, wherein
- the inner expandable stent has a second plurality of cells formed by a second plurality of interconnected strut members; the second plurality of removable slat members are interwoven between said second plurality of strut members; and
- the first and second plurality of tethers are detachable.

7. A vascular medical device comprising:
- an expandable stent which takes the form of a hollow tubular member comprised of an expandable wire frame having a peripheral surface;
- a plurality of elongated removable slat members carried by said hollow tubular member and providing a substantially continuous cover for the peripheral surface of said hollow tubular member such that said substantially continuous cover impedes the flow of blood through the peripheral surface of said medical device when deployed within a blood vessel, wherein each slat member has a circumferential width greater than its wall thickness; and
- a plurality of tethers attached to each of said removable slat members so that one of said tethers may be pulled to remove one of said slat members from said hollow tubular member to re-establish patency in a branching vessel while impeding blood flow through other portions of said medical device.

8. The vascular medical device as defined in claim 7, wherein said tethers are removably attached to said removable slat member.

9. The vascular medical device as defined in claim 7, wherein said tethers are comprised of a bioabsorbable material.

10. The vascular medical device as defined in claim 7, wherein each of said tethers takes the form of an elongated puller wire.

11. A method of treating an aneurysm comprising the steps of:
- (a) providing an expandable stent which takes the form of a skeletal tubular member having a peripheral surface and a plurality of removable slat members each carried by said skeletal tubular member to provide a substantially continuous cover for said peripheral surface, wherein each slat member has a circumferential width greater than its wall thickness;
- (b) inserting said expandable stent into a blood vessel of a patient;
- (c) advancing said expandable stent through said blood vessel until said expandable stent is aligned with and covering an aneurysm in said blood vessel such that said substantially continuous cover impedes the flow of blood through the peripheral surface of said expandable stent when deployed within a blood vessel; and
- (d) selectively removing one or more of said plurality of removable slat members by moving the tether attached to said removable slat member proximally and thus allowing blood flow to a branching blood vessel.

12. The method of treating an aneurysm as defined in claim 11, wherein said step (a) further comprises:
- an inner expandable stent which takes the form of a second skeletal tubular member which defines a second peripheral surface, a second plurality of removable slat members carried by said second skeletal tubular member to provide a substantially continuous cover for said second peripheral surface, and a second plurality of tethers each attached to one of said second plurality of slat members, said inner expandable stent being coaxially disposed within said expandable stent and positioned such that said pluralities of removable slat members form a substantially continuous cover for said medical device, wherein each slat member has a circumferential width greater than its wall thickness.

* * * * *